United States Patent
Roy et al.

(10) Patent No.: US 10,465,244 B2
(45) Date of Patent: Nov. 5, 2019

(54) ELECTROCHEMICAL DNA BIOSENSOR USING GRAPHENE BIOCHIP FOR SPECIES IDENTIFICATION

(71) Applicants: Sharmili Roy, Gadong (BN); Ibrahim Abdul Rahman, Jalan (BN); Minhaz Uddin Ahmed, Jalan (BN)

(72) Inventors: Sharmili Roy, Gadong (BN); Ibrahim Abdul Rahman, Jalan (BN); Minhaz Uddin Ahmed, Jalan (BN)

(73) Assignee: Universiti Brunei Darussalam, Gadong (BN)

( * ) Notice: Subject to any disclaimer, the term of this patent is extended or adjusted under 35 U.S.C. 154(b) by 501 days.

(21) Appl. No.: 14/968,774

(22) Filed: Dec. 14, 2015

(65) Prior Publication Data

US 2016/0177387 A1    Jun. 23, 2016

Related U.S. Application Data

(60) Provisional application No. 62/092,873, filed on Dec. 17, 2014.

(51) Int. Cl.
*C12Q 1/68* (2018.01)
*G01N 27/30* (2006.01)
(Continued)

(52) U.S. Cl.
CPC ......... *C12Q 1/6876* (2013.01); *C12Q 1/6834* (2013.01); *G01N 33/12* (2013.01); *G01N 27/308* (2013.01)

(58) Field of Classification Search
None
See application file for complete search history.

(56) References Cited

U.S. PATENT DOCUMENTS

| | | | | |
|---|---|---|---|---|
| 2004/0086894 | A1* | 5/2004 | Crothers | C12Q 1/682 435/6.11 |
| 2006/0008818 | A1* | 1/2006 | Chem | B01J 19/0046 435/6.11 |

(Continued)

OTHER PUBLICATIONS

Ahmed et al., Analyst, vol. 138, pp. 907-915, published Nov. 19, 2012.*

*Primary Examiner* — Robert T. Crow
(74) *Attorney, Agent, or Firm* — Geeta Kadambi; Riddhi IP LLC (57) ABSTRACT

This study describes about a new electrochemical biosensor using DNA-redox electrostatic interaction and their subsequent non-specific adsorption on graphene screen-printed electrode or biochip. The ruthenium hexamine molecule $[Ru(NH_3)_6]^{3+}$, or RuHex, was observed to form complexes with free DNA in solution that adsorbed onto graphene surfaces, enabling the development of a rapid, high-sensitivity DNA biosensor. Reproducible cathodic current signals were generated from these low-cost graphene biochips, both in the presence and absence of dsDNA and loop-mediated isothermal amplification (LAMP) amplicons. The combination of the DNA-redox molecule complexes and the graphene surface therefore provided a novel detection strategy. This new biosensor was able to identify different meat species based on the isothermal amplification of target genes followed by electrochemical detection with square wave voltammetry.

9 Claims, 6 Drawing Sheets

Specification includes a Sequence Listing.

(51) Int. Cl.
*C12Q 1/6876* (2018.01)
*G01N 33/12* (2006.01)
*C12Q 1/6834* (2018.01)

(56) References Cited

U.S. PATENT DOCUMENTS

| | | | |
|---|---|---|---|
| 2009/0036315 A1* | 2/2009 | Labgold | G01N 33/54306 506/1 |
| 2009/0278556 A1* | 11/2009 | Man | G01N 27/4146 324/693 |
| 2012/0003661 A1* | 1/2012 | Eckert | C12Q 1/04 435/6.15 |

* cited by examiner

ELECTROCHEMICAL DNA BIOSENSOR USING GRAPHENE BIOCHIP FOR SPECIES IDENTIFICATION

CROSS REFERENCE TO RELATED APPLICATIONS

This application claims priority to a Provisional Application 62/092,873 filed on Dec. 17, 2014 in USA and is hereby incorporated by reference in its entireties for all of its teachings. This application contains sequence listing that has been submitted as named PRIMERDATA_ST25.txt, the date of creation Jan. 29, 2016, and the size of the ASCII text file in bytes is 2 kb.

FIELD OF INVENTION

The instant application discloses a novel method for identifying species in food sources using a DNA-Redox interaction on graphene nanomaterial as a novel electrochemical biosensor is described.

BACKGROUND

Food adulteration and food contamination are two very big issues that is encountered in most developing countries. It effects health and violates religious beliefs of the consumer. There is plethora of methods available to detect this contamination but it takes a long time to get the results back. There is a need for more sensitive and fast process.

SUMMARY

The present disclosure relates to a method of identifying a species in a food source using a graphene biosensor. Further, the present disclosure relates to a method of identifying a meat species in a food source by DNA-Redox electrostatic interaction. Thus, the instant disclosure describes a method of DNA detection using DNA-Redox interaction on graphene nanomaterial.

In one embodiment, the biosensor comprises of a ruthenium hexamine molecule $[Ru(NH_3)_6]^{3+}$ or RuHex, wherein RuHex is adsorbed onto the graphene surface. In another embodiment, RuHex forms complex with free DNA or amplicon present in food enabling development of high-sensitive DNA biosensor such as the disclosed graphene biosensor.

In one embodiment, the biosensor can identify different species based on isothermal amplification of target genes. In another embodiment, the isothermal amplification is followed by electrochemical detection with square wave voltammetry (SWV). In some embodiments, a specific primer has been designed for each species such as a specific primer for chicken and pork.

In one embodiment, a method to amplify the species of interest using a novel primer design is being described. In another embodiment, a loop mediated isothermal amplification (LAMP) method is used for amplification of amplicon using the novel primer designed for the said species. Thus, electrochemical analysis of species is conducted by means of SWV using RuHex complex and adding the LAMP products to graphene electrodes.

In one embodiment, functioning of graphene biosensor to detect species in a food source is disclosed. In another embodiment, the method discloses that in the absence of double stranded DNA (dsDNA) i.e. absence of any species with DNA in a food source, the RuHex yields a significant lower current due to slow dissolution of RuHex whereas, in the presence of dsDNA, the RuHex yields a significantly higher current which is then detected by graphene biosensor and hence shows presence of a species in the tested food source. When electrostatic interaction occurred between ds DNA and redox on the graphene surface then due to the strong binding of these two components and to the close proximity of RuHex to the graphene surface results faster diffusion currents which produced a higher cathodic current. In the absence of dsDNA, the redox component yielded a significantly lower reduction current due to the slow dissolution of RuHex as it is not close to the electrode surface.

In one embodiment, a method of using a graphene biosensor to detect a species in a food item is disclosed, comprises: synthesizing a primer specific for the species to be detected; preparing a ruthenium hexamine molecule $[Ru(NH_3)_6]^{3+}$ (RuHex) solution; placing the RuHex mixture onto the graphene biosensor; contacting the graphene biosensor with the food item to be tested and forming a system; and detecting the cathodic current which may be produced by applying square wave voltammetry (SWV) to the system, wherein a high cathodic current is produced when RuHex moves in close proximity to graphene biosensor due to RuHex binding with the DNA of the species in the food item indicating presence of species in the food item. In another embodiment, a low cathodic current is produced when RuHex does not moves in close proximity to graphene biosensor due to RuHex non-binding with the DNA of the species in the food item indicating that there is no species in the food item.

In one embodiment, a method of using a graphene biosensor to detect a meat species in a food item is disclosed, comprises: synthesizing a primer specific for the species to be detected; preparing a ruthenium hexamine molecule $[Ru(NH_3)_6]^{3+}$ (RuHex) solution; placing the RuHex mixture onto the graphene biosensor; contacting the graphene biosensor with the food item to be tested and forming a system; and detecting the cathodic current which may be produced by applying square wave voltammetry (SWV) to the system, wherein a high cathodic current is produced when RuHex moves in close proximity to graphene biosensor due to RuHex binding with the DNA of the meat species in the food item indicating presence of species in the food item. In another embodiment, a low cathodic current is produced when RuHex does not moves in close proximity to graphene biosensor due to RuHex non-binding with the DNA of the species in the food item indicating that there is no meat species in the food item.

In most embodiments, the DNA is detected using agarose gel method or other known methods. Further, a primer design for development of LAMP of porcine gene for a sensitive assay is also developed.

In one embodiment, a food contamination to detect the cross contamination or falsification of a said meat species is developed. In another embodiment a chicken and pork contamination detection process is being shown.

The disclosed biosensor help achieving a detection limit of 1 pg/µL to 100 pg/µL.

In one embodiment, a short method to isolate, amplify; combine with asymmetric hydrogenation catalysts based on ruthenium and biochip made up of graphene. Other features will be apparent from the accompanying drawings and from the detailed description that follows.

BRIEF DESCRIPTION OF DRAWINGS

The embodiments of this invention are illustrated by way of example and not limitation in the FIGS. of the accompanying drawings, in which like references indicate similar elements and in which:

FIG. 1A, FIG. 1B, FIG. 1C and FIG. 1-D shows the principle of DNA detection in the solution using carbon electrodes (FIG. 1A and FIG. 1B) and graphene electrodes (FIG. 1C and FIG. 1D). FIG. shows free RuHex solution as adsorbed on carbon (FIG. 1A) and graphene (FIG. 1C) electrode and DNA-RuHex interaction wherein DNA-RuHex diffuses slow on carbon electrode surface (FIG. 1B) as compared to diffusion on graphene electrode (FIG. 1D).

All labels in the attached Figures are abbreviated to FIG. instead of Figure as shown in the description. Other features of the present embodiments will be apparent from the detailed description that follows.

DESCRIPTION

A variety of diagnostic technologies have been developed to achieve rapid detection and identification of various pathogens. In recent years, food adulteration has become a major concern in the food industry as well as amongst consumers. It is now common for high quality raw materials to be substituted with inferior and cheaper substances. Although numerous analytical methods have been used for pork analyses, isothermal amplification of target DNA and its integration with portable sensors could tap into market potential for routine applications as point-of-care (POC) diagnostics (Craw et al., 2012).

In recent years, loop-mediated isothermal amplification (LAMP) has been the most widely explored nucleic acid (NA) detection strategy because of its high sensitivity and specificity. LAMP was first described by Notomi et al. (2000). The main principle of LAMP is based on auto-cycling strand displacement DNA synthesis by the Bst DNA polymerase exonuclease-negative large fragment under isothermal conditions, within a relatively short period of time (Grab et al., 2005). The LAMP strategy can amplify up to $10^9$ copies in less than one hour because of the use of six primers that recognize different sequences of the target DNA with high specificity (Fukuta et al., 2003).

In recent years, DNA analysis has emerged as one of the most current and challenging applications of electrochemical sensors. Voltammetry sensors, such as those based on differential pulse voltammetry, square wave voltammetry and linear sweep voltammetry can be used to determine the concentration effects of analytes on a biosensor by measuring the cathodic peak height of reactions with high sensitivity. In electrochemical DNA biosensors, single strand DNA (ssDNA) probes are generally immobilized onto the surface through the pre-treatment of the biosensors. A number of modifications such as nanoparticles and conducting polymers have been used for this purpose (Peng et al., 2004). Hybridization between the probe and target DNA is then used to generate reproducible voltammetric and impedimetric electrochemical signals, through their interaction with an active redox compound. However, these redox molecules interact with both double- and single-stranded DNA, producing contradictory results that pose a significant limitation for nucleic acid hybridization-based sensors.

As an alternative to hybridization-based sensors, Ahmed and coworkers used carbon-based working and counter electrodes with the ruthenium hexamine (RuHex) molecule as a redox indicator for loop amplicon detection (Ahmed et al., 2012).

From our previous research, when RuHex binds to LAMP amplicons it gives rise to an electrochemical signal (Ahmed et al., 2009). The strength of this signal decreases upon interaction of these complexes with carbon electrode surfaces, due to DNA-RuHex complexes diffusing away from the electrode surface. The advantages in using RuHex lie in its high charge and versatile capacity for binding to DNA.

According to Rich and coworkers, RuHex lacks intercalating ligands and binds instead in an electrostatic manner to the anionic DNA backbone (Ho et al., 1987).

Graphene has attracted wide research interest because of its unique and simple physical properties (Watanabe et al., 2011; Novoselov et al., 2004). Graphene is the newest class of carbon nanomaterials with nanoscale properties in one dimension (one-atom-thickness) with exceptional electronic, optical and mechanical properties and a high surface area, as well as being robust in nature (Chua et al., 2013; Schniepp et al., 2006). In recent years, graphene has been used in building DNA-based optical sensors for the detection of nucleic acids, proteins, viruses, small molecules and metal ions (Lim et al., 2014).

In our recent observations, in contrast with carbon electrode surfaces, RuHex provides higher and more reproducible signals on graphene material in the presence of dsDNA compared with those of non-DNA complexes (Ahmed et al., 2009). We observed that the nonspecific adsorption of the graphene material by DNA, which occurs through pi stacking, actually brought the RuHex in close proximity to the graphene biosensor surface via DNA-RuHex electrostatic interactions (FIG. 1A-1D). Upon applying voltage by means of square wave voltammetry (SWV), the resulting faster diffusion currents produced a higher cathodic current due to the close proximity of RuHex to the graphene surface. In the absence of dsDNA, the RuHex yielded a significantly lower reduction current due to the slow dissolution of RuHex. This new electrochemical biosensor strategy has been used here for the first time to detect isothermal amplicons of meat species as a model system, where picogram levels of the starting materials were used as template DNA. RuHex itself is a charged carrier, and using the chronocoulometric (CC) test we therefore observed higher charge signals in the presence of dsDNA compared with RuHex in the absence of DNA bound to the graphene surface. The terms biochip and biosensors are used interchangeably throughout the application.

Methods and Material

Reagents and Chemicals: Hexaammineruthenium(III) chloride—$Ru(NH_3)_6Cl_3$ or RuHex complex, was obtained from Sigma-Aldrich (MO, USA). We prepared 200 µM RuHex solutions in water and stored the solutions at 4° C. Tris-HCl (pH 7.4) was prepared using Trizma base purchased from Vivantis Technologies (Selangor, Malaysia). Deoxyribonucleic acid sodium salt from salmon testis was purchased from Sigma-Aldrich (MO, USA). All chemicals were of analytical grade purity. All solutions were prepared and diluted using ultra-pure (18.3 M'Ω) water. The concentration and purity of DNA were estimated with UV/Vis spectrophotometry, using a NanoPhotometer (Implen GmbH, Germany).

Sample extractions and LAMP assays: Salmon DNA obtained from Sigma-Aldrich was diluted with TE (Tris-EDTA) Buffer for further experiments. All other meat species were collected as food samples from different local markets of Brunei Darussalam (Table 1) and their DNA were extracted using the DNeasy®) tissue kit (Qiagen®, Germany). LAMP reactions were prepared in polypropylene tubes in a 25-µL reaction volume comprising 1×reaction mix with 3 mM $MgSO_4$ (New England Biolabs, MA, USA), 0.64 M betaine (Sigma-Aldrich), 0.4 mM dNTP (New England Biolabs), 0.2 µM each of the F3 and B3 primers, 1.6 µM each of the FIP and BIP primers, 0.8 µM each of the LF and LB primers (Integrated DNA Technologies, Coralville, USA), 16 U of the Bst (*Bacillus stearothermophilus*) DNA polymerase large fragment (New England Biolabs), 2.5 µL of 10× ThermoPol® Reaction Buffer (New England Biolabs) and 5 µL of target genomic DNA. To avoid evaporation, 10 µL of mineral oil was used to overlay each solution.

Five different sets of pork primers and seven different sets of chicken primers were tested for the best primer combination prior to further optimization of the electrochemical sensor. The sequences of the LAMP primers for pork (*Sus scrofa*) and chicken (*Gallus gallus domesticus*) species are shown in Table 2 and were designed using Primer Explorer V 3.0 (Eiken Chemical Co., Ltd., Japan). LAMP reactions were carried out at temperatures ranging from 60 to 65° C. and for different time periods of up to 60 min. The amplified LAMP products (2 µL) were analyzed by 2% agarose gel electrophoresis and stained with ethidium bromide.

TABLE 1

Commercially processed foods along with their types of species, as labeled.

| Food Type | Species (as labeled) |
|---|---|
| Pork sausages | *Sus scrofa* |
| Curry mutton | *Puffinus tenuirostris* |
| Corned beef | *Bos taurus* |
| Chicken luncheon meat (Singapore) | *Gallus gallus* |
| Chicken luncheon meat (Malaysia) | *Gallus gallus* |
| Chicken randang* | *Gallus gallus* |
| Canned pork | *Sus scrofa* |
| Mock curry mutton | *Puffinus tenuirostris* |
| Pork luncheon meat | *Sus scrofa* |
| Chicken luncheon meat | *Gallus gallus* |

*Randang: Rendang is a meat dish in Borneo region that is slow-cooked in coconut milk.

TABLE 2

Sequences of LAMP Primer of the pork and chicken species.

| Species | Primers | Type | Sequences |
|---|---|---|---|
| Chicken | F3 (SEQ ID No: 1) | Forward outer | 5'GCCCCATCCAACATCTCTG 3' |
|  | B3 (SEQ ID NO: 2) | Backward outer | 5' CGTTTGCGTGGAGATTCCG 3' |
|  | FIP (SEQ ID NO: 3) | Forward Inner | 5'-ATGGCTAGTAGTAGGCCG-GTGA-TTCGGCTCCCTATTAGCAGT 3' |
|  | BIP (SEQ ID NO: 4) | Backward Inner | 5'-CACAGCAGACACATC-CCTAGCC-TCAGCCGTATTGTACGTTCC 3' |
|  | LF (SEQ ID NO: 5) | Loop Forward | 5'-GGATTTGGGTCATGAG-GCAG 3' |
|  | LB (SEQ ID NO: 6) | Loop Backward | 5'TTCTCCTCCTCCGTAGCCCACA 3' |
| Pork | F3 (SEQ ID NO: 7) | Forward outer | 5' ATCATTCTGAGGAGCTACG 3' |
|  | B3 (SEQ ID NO: 8) | Backward outer | 5' TTGTTGGATCCGGTTTCG 3' |

TABLE 2-continued

Sequences of LAMP Primer of the pork and chicken species.

| Species | Primers | Type | Sequences |
|---|---|---|---|
| | FIP (SEQ ID NO: 9) | Forward Inner | 5'-AAGCCCCCTCAGATTCATTC-TAC-GTCATCACAAATCTAC-TATCAGC 3' |
| | BIP (SEQ ID NO: 10) | Backward Inner | 5'-CAAAGCAACCCTCACAC-GATTC-TATGAGATGTACGGCTGC 3' |
| | LF (SEQ ID NO: 11) | Loop Forward | 5'AGGTCTGTTCCGATATAAGGAT 3' |
| | LB (SEQ ID NO: 12) | Loop Backward | 5' CGCCTTCCACTTTATC-CTGC 3' |

Electrochemical Detection: For electrochemical detection we used SWV method for its faster signal acquisition and increased sensitivity, as compared to other electrochemical methods. The disposable carbon graphene-modified working SPEs were obtained from DropSens (Asturias, Spain) and were made up of a carbon counter-electrode and a silver reference electrode. The biosensors were prepared with a ceramic substrate with the dimensions 33×10×0.5 mm (LWH).

SWV Procedure: Square wave voltammetry was used for all electrochemical studies on the eDAQ electrochemical analysis system with EChem software (eDAQ Pty Ltd., NSW, Australia). A RuHex stock solution (1 mM) was prepared by directly dissolving it in high purity water (p=18.3 MΩ cm), and further dilutions were prepared in water to reach a final concentration of 12.5 µM. The conditions for SWV were as follows: frequency=25 Hz; amplitude=49.5 mV, scan rate=48.75 mV $5^{-1}$; and step potential=1.95 mV. The current responses from the reaction mixture including RuHex were recorded and scanned in the range of −0.1 to −0.5 V. Throughout the experiment, 50 µL of the sample mixture was placed onto the graphene biosensor which was then scanned for cathodic peak currents. The changes in the current responses were recorded and processed using the integrated software of the Edaq system. All experiments were carried out at ambient laboratory temperature (23-25° C.). For the CC test we used the compact Autolab system PGSTAT101 III (Metrohm, The Netherlands) in conjunction with its Nova 1.10 software. All data are represented as an average of at least three replicates.

Results and Discussion

DNA analysis is one of the most current and challenging application of electrochemical sensors. Voltammetric sensors (SWV) determined the concentration effects and sensitivity of the analytes on biosensor, and measured the cathodic peak height of a specific reaction. In previous study, Ahmed and his co workers used carbon based working and counter electrodes with RuHex, as a redox indicator, for loop amplicon detection. Kivlehan and his co-workers used helicase-dependent amplification (HDA) based amplification for real-time electrochemical detection of <100 bp DNA sequences from an E. coli plasmid, using [(bpy)$_2$DPPZ$_2$+(O$_s$)] as a redox indicator. However, HDA is limited to DNA amplification of targets smaller than 200 bp, and it was nearly impossible to work with billion by genomic DNA.

In this study, DNA-redox electrostatic interactions and their non-specific adsorption on graphene biosensor was observed, using pork and chicken as model species for detection at picogram level. This approach was simple, quick, new, cost effective and easy to operate. On the other hand, LAMP was more robust, sensitive and rapid than other nucleic acids amplification strategies. Moreover, using RuHex as a redox mediator, with its binding affinity of $1.2 \times 10^6$ M$^{-1}$ for DNA, permitted us to apply it for electrochemical detection using LAMP amplicon.[37] At the beginning, we performed SWV on free RuHex and the RuHex-salmon dsDNA, in order to determine the individual electrochemical redox reaction on different concentrations. We observed the increased peak pattern in graphene biosensor with higher doses of salmon DNA, that was an opposite trend compared to the behavior on carbon electrodes.

Figure 3:
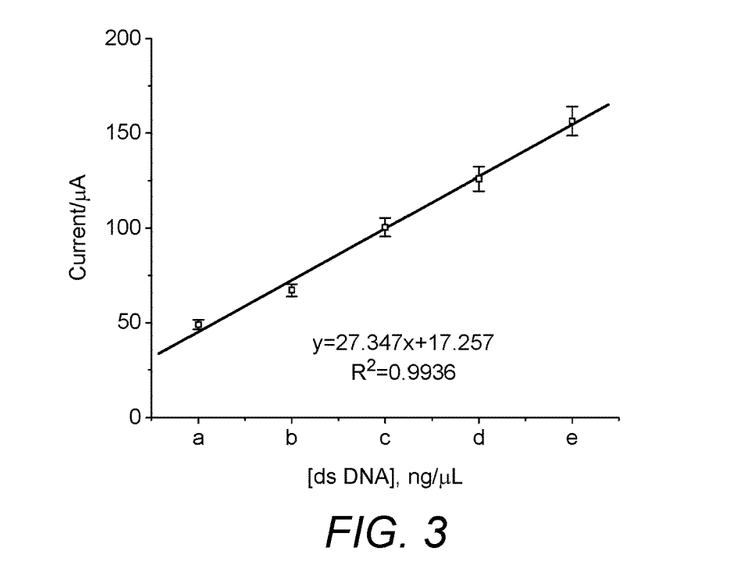
FIG. 3 shows dose-Response curve for the determination of 0-80 ng/μL salmon dsDNA using 12.5 μM RuHex on graphene biochip: (a) 0 ng/μL, (b) 10 ng/μL, (c) 20 ng/μL, (d) 40 ng/μL, and (e) 80 ng/μL of DNA concentrations. SWV was used as a detection mode transducer. Error bars indicate the standard deviation of at least three repeated measurements.
Figure 4:
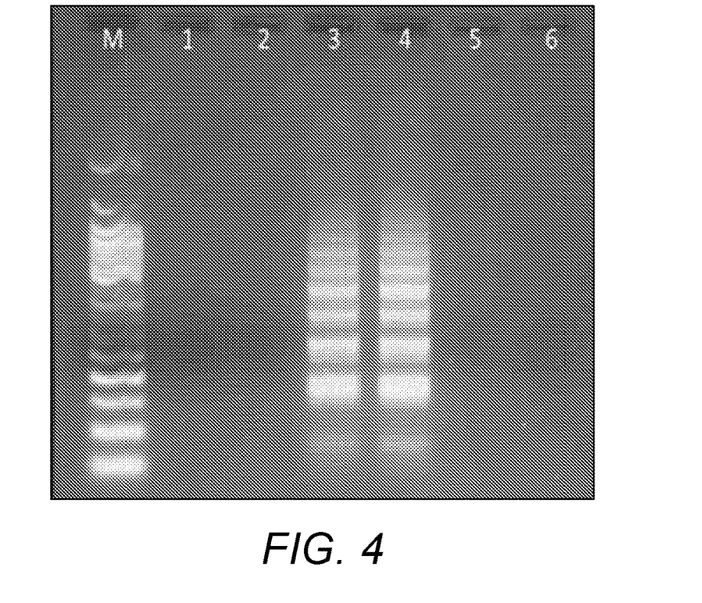
FIG. 4 shows gel electrophoresis analysis of the LAMP amplified products. This study was performed using pork primers as shown on (Table 2) and LAMP products were run on a 2% agarose gel. Lane M, 50 bp ladder used as a marker, lane 1 and 2, Non target control with TE-Buffer; lane 3 and 4, LAMP amplified product of pork template DNA; lane 5 and 6, LAMP amplified product of chicken DNA (non specific target). The gel was stained with ethidium bromide.

Initial Optimization with Salmon dsDNA: Using RuHex as a redox mediator, with its binding affinity of $1.2 \times 10^6$ M$^{-1}$ for DNA, enables the electrochemical detection of LAMP amplicons on surfaces such as graphene. To validate and characterize the mechanism of this new electrochemical detection strategy, SWV-based detection was performed initially on graphene biosensor surfaces bound with RuHex alone (12.5 µM), or with RuHex complexed with a range of salmon dsDNA concentrations (10-80 ng/µL). We observed increasing cathodic peak signals with increasing concentrations of salmon DNA (correlation coefficient of 0.9936; FIG. 3), which is the inverse of the trend observed for carbon electrodes (Ahmed et al., 2012). In the absence of DNA, a significantly lower cathodic peak was observed. The cathode current was higher in the presence of DNA due to the proximity of the redox species to the electrode surface, which arose from the non-specific adsorption of the DNA-RuHex complexes on the graphene surface (Steel et al., 1988). In our method we used isothermal DNA amplicons onto the electrode surface, which is already specified and sorted with specific primers. We have further tested using gel electrophoresis to confirm the specific DNA amplicons on agarose gel (FIG. 4). Positive bands showed the specific amplifications with specific primers and non-specific amplicons showed no bands on the gel.

Figure 8A:
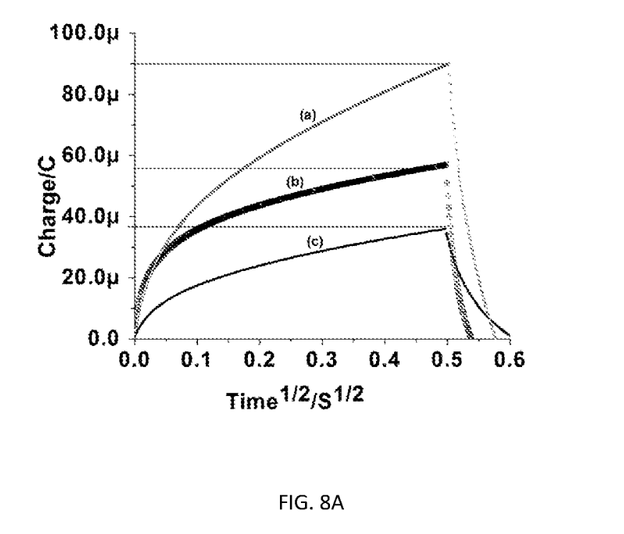
FIG. 8A and 8B. An increased response was observed for RuHex alone relative to the treatment with buffer only, due to the charge associated with the RuHex molecules.
Figure 8B:
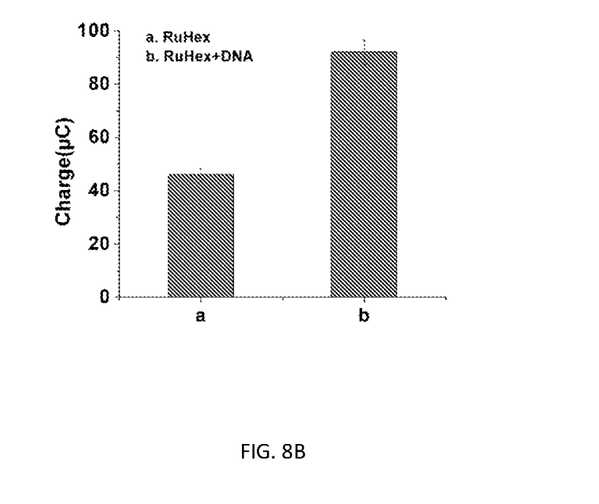

CC Test on Salmon DNA: To observe the surface charge, the CC tests for RuHex, in presence/absence of DNA on graphene surface, was also performed and were shown in the FIGS. 8A and 8B. An increased response was observed for RuHex alone relative to the treatment with buffer only, due to the charge associated with the RuHex molecules. However, for RuHex in the presence of salmon dsDNA, even higher signals were observed due to the electrostatic interaction between RuHex and the DNA and the nonspecific adsorption of the RuHex-dsDNA complexes on the graphene surface. In this experiment, dsDNA was used as the analyte; however, we also tested only primer products which contains ssDNA but the concentrations of the ssDNA were very low (data not shown), resulting in similarly low signals 50 µA, while amplicon dsDNA produced signals of ~120 µA. The concentration of ds DNA is higher than ss DNA which makes the difference between two signals coming from each DNA. Therefore, there should not be any chance of mixing or interfering of ss DNA and ds DNA.

Optimization of LAMP assays condition: Initially LAMP was optimized and standardized for chicken and pork species detection, by using their specific primers (Table 2). DNA was extracted from different types of processed foods using Qiagen®kit. The food samples were collected from the local supermarkets and some were imported from neighboring countries. For optimizing the LAMP condition, different temperatures and concentration of reagents (as mentioned in materials and methods section) were used to get positive and reproducible amplifications (amplicons) for particular primers. Chicken primers were used to amplify the chicken DNA template under different isothermal conditions. The specific amplifications generated the ladder-like pattern of bands on 2% agarose gel. In this study, we tested a total of 7 different sets of chicken primers where each set comprised six sequences. For each set the above parameter optimization was performed, and optimal amplification for chicken species detection was determined to occur at 60° C. with a limit of detection (LOD) of 1 pg/µL (Table 3). A cross-reactivity test was also performed with pork, mutton and beef samples to confirm the specificity of the chicken primers so as to avoid non-specificity. The amplifications showed the typical LAMP ladder-like pattern for the chicken samples, while no such pattern was observed for the other species, thereby confirming the specificity of the chicken primers and the associated LAMP protocol (data not shown).

Further, five sets of pork primers and other protocol parameters were also optimized to find the best suitable combinations with their highest sensitivity and seamless reproducibility. The optimal and best primers were used to amplify traces of pork DNA under isothermal conditions of 63° C. using reaction conditions as mentioned in Table 3. In addition, LAMP reaction was performed with detection ranging from 1000 pg/µL-1 pg/µL of the pork extracted DNA, and the amplicon was found with the initial DNA conc. was 100 pg/µL. To check the cross contamination with other species such as pork primers with other species, LAMP was performed using genomic DNA of chicken (FIG. 4). FIG. 4 shows the ladder-like pattern which was of pork species-specific amplicon, using pork specific primers. On the other side, no positive amplicon pattern was observed using the same primers and with the chicken DNA. The low LOD obtained validated the use of our pork species-specific primers for the detection of target DNA at low concentrations.

Figure 5A:
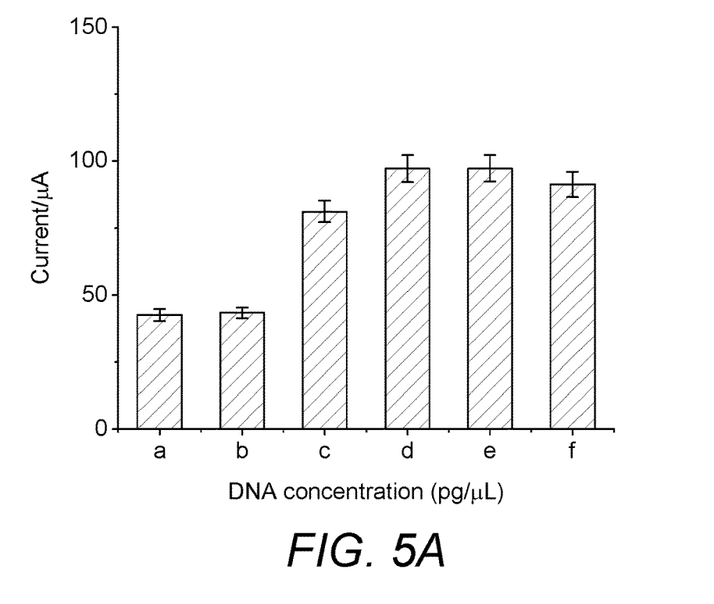
FIG. 5A shows SWV measurements with RuHex and chicken LAMP amplicons, indicated the limit of detection of chicken 1 pg/μL. Where (a) buffer and RuHex, (b) buffer/RuHex/negative control, (c) buffer/RuHex/LAMP positive 1000 pg, (d) buffer/RuHex/LAMP positive 500 pg, (e) buffer/RuHex/LAMP positive 100 pg, and (f) buffer/RuHex/LAMP positive 1 pg, were loaded on graphene biosensor.
Figure 5B:
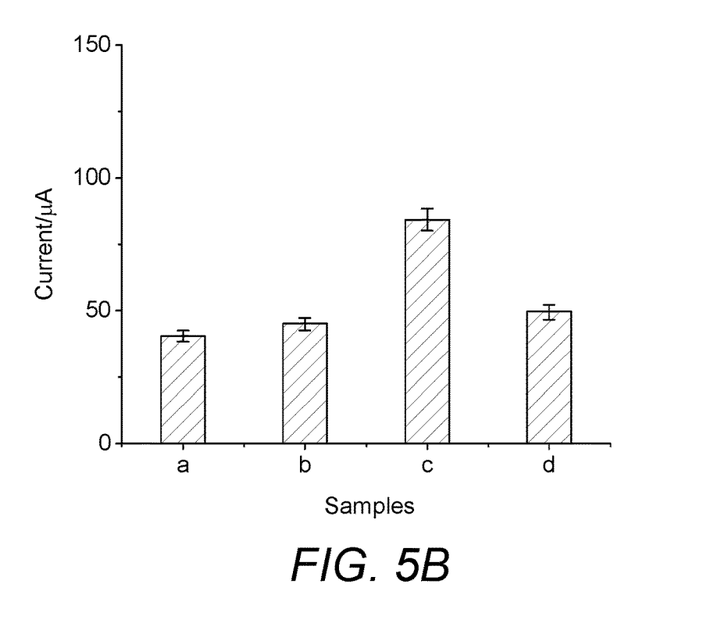
FIG. 5B shows testing the cross reactivity of the chicken and pork species with chicken primer where (a) buffer/RuHex, (b) Buffer/RuHex and LAMP negative control, (c) RuHex/chicken LAMP products, and (d) RuHex/pork LAMP products, were loaded respectively onto the biosensor. Error bars indicate the standard deviation of at least three replicates. The measurements showed higher cathodic peak signal for chicken specific template DNA and their associated LAMP products.

We used two loop primers pork and chicken to detect the species respectively. We diluted DNA ranging from 1000 pg to 1 pg and thereafter we amplified those DNA and measured the signals by electrochemical analysis (FIGS. 5A and 5B). We found that the current differences between different concentration of DNA amplicons which helps to know the limit of detection for chicken and pork species. The limit of detection estimated from the mean value of three repetitive experimental values. Blank and all negative samples serves the current range from 1-50 µA (FIG. 5 A) whereas, while measuring the samples it shows the current 120 µA. Hence analyzing the graph visually we can evaluate the minimum amount of meat species as limit of detection.

TABLE 3

Result of LAMP amplification under different isothermal condition and limit of detection, on each detection.

| | Amplification condition and details | | |
|---|---|---|---|
| Primers | Amplification conditions | LOD | Cross reactivity |
| Chicken primer | Temperature = 60° C.<br>MgSO$_4$ = 3 mM<br>dNTPS = 0.4 mM | 1 pg/µL | None |
| Pork primer | Temperature = 63° C.<br>MgSO$_4$ = 3 mM<br>dNTPS = 0.4 mM | 100 pg/µL | None |

Figure 6A:
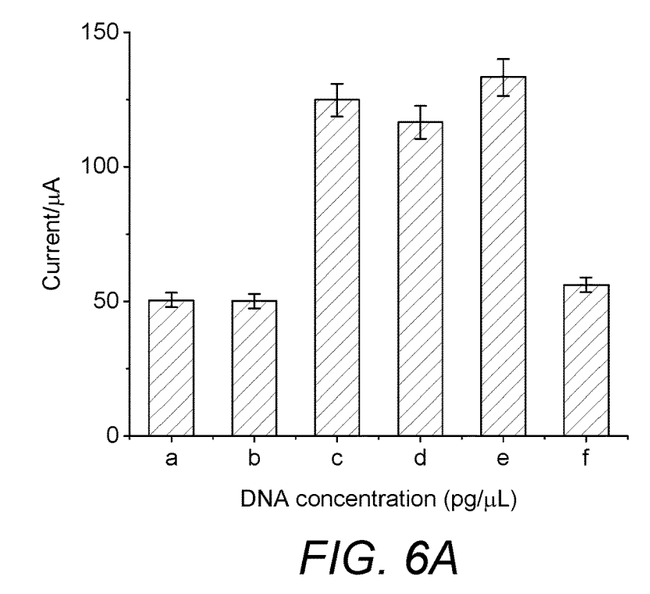
FIG. 6A shows SWV measurements for (a) buffer and RuHex only, (b) buffer, RuHex and LAMP-negative control solution, (c) buffer, RuHex and LAMP-positive products for 1000/μL pg template, (d) buffer, RuHex and LAMP-positive products for 500 pg/μL template, (e) buffer, RuHex and LAMP-positive products for 100 pg/μL template, and (f) buffer, RuHex and LAMP-positive products for 1 pg/μL template.
Figure 6B:
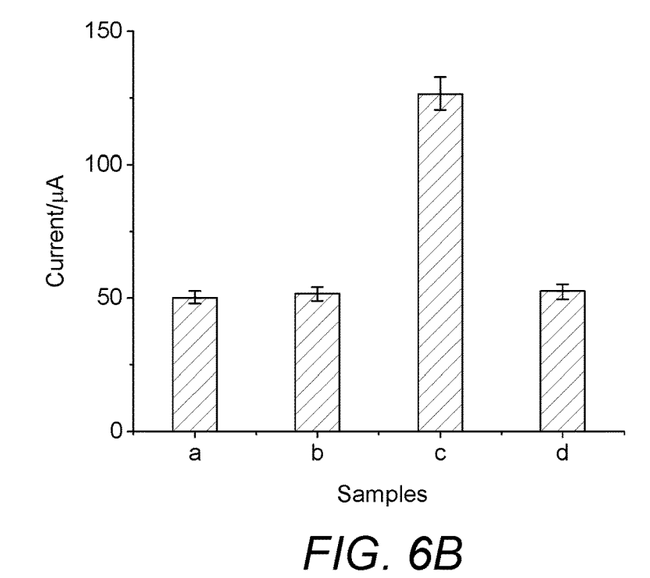
FIG. 6B shows testing the cross reactivity of the pork loop primer towards chicken species where (a) buffer and RuHex, (b) buffer, RuHex and LAMP-negative control solution, (c) RuHex and pork LAMP products, (d) RuHex and chicken LAMP products, were loaded onto the biochip, respectively. Error bars indicate the standard deviation of at least three replicates. The measurements showed higher cathodic peak signal for pork specific template DNA and their associated LAMP products.

Electrochemical Detection of LAMP Amplicon: LAMP amplicons of sample DNA with the chicken and pork species specific primers, mixed the LAMP products with RuHex molecules and added the DNA-RuHex complexes to the graphene biosensor to measure the resulting signals by SWV electrochemical analysis. Agarose gel analysis was performed to correlate the electrochemical detection of the amplicons. We observed that by diluting the target DNA between 1 and 1000 pg/µL, the current differences between the different concentrations of amplicons enabled the accurate determination of the LOD for both the chicken and pork species (FIGS. 5A-B and 6A-B). After LAMP amplification was carried out in a polypropylene tube using a heat block, 5 µL of product was mixed with RuHex and Tris-HCl buffer, and then spiked on the biosensor surface for electrochemical measurement. In case of chicken species, the limit of detection of template DNA was 1 pg/µL, therefore, the cathode signal showed higher peak current with the initial chicken DNA concentration from 1000 to 1 pg/µL (FIG. 5A). In FIG. 5B, it is shown that the peak current was higher when only chicken DNA was used as a template. Low peak current showed no amplicon production due to the use of chicken specific primers, which could only amplify the chicken DNA but not the non-target control (water) and other species. On the other hand, using the same protocol but with different primers and temperature range, we could achieve the sensitivity up to 100 pg/µL of pork DNA (FIG. 6A). Therefore, it can be referred that the LOD of pork is up to 100 pg/µL, with this primer combination and detection platform. Agarose gel analysis of the LAMP products was also performed for correlation (data not shown). FIGS. 5 and 6 shows that different concentrations of template DNA were used to detect chicken and pork respectively, as mentioned in the materials and methods. After LAMP amplification was carried out in a polypropylene tube using a heat block, 5 µL of product was mixed with RuHex and Tris-HCl buffer, and then spiked on the biosensor surface for electrochemical measurement. Limit of detection of loop amplified target DNA by electrochemical sensor was derived by preparing different dilution of sample ranging between 1000 pg/µL to 1 pg/µL.

In the case of chicken species identification, the LOD for the template DNA was 1 pg/µL (FIG. 5A), and no significant cross-reactivity with pork template DNA was observed with the chicken primers (FIG. 5B). The low peak current for the pork template DNA reflected the high specificity of the chicken primers, which were only observed to produce amplicons from the chicken DNA but not from the non-target control (water) or the pork DNA. The LOD was similarly determined for pork template DNA, using the same protocol but with pork-specific primers and a different isothermal amplification temperature. A LOD of 100 pg/µL for pork template DNA was achieved (FIG. 6A), and no cross-reactivity with chicken template DNA was observed (FIG. 6B). It is shown that the peak current was higher while only the pork DNA was used as a template. Low peak current showed no amplicon production due to the use of pork primers. Like 4B, non-target control (water) and a cross species could not be amplified.

To design both of these loop primer sets for pork and chicken, we used mitochondrial cytochrome b gene. (gene bank accession number: X56295.1). We hypothesize that the sensitivity obtained with the chicken loop primers and pork loop primers was attributable to the capacity of these primers to efficiently amplify up to 1 pg/µL and 100 pg/µL respectively. In optimizing the sensitivity of LAMP, more emphasis have been put on testing of several primer pairs than on the extensive screening of reaction parameters (He et al., 1994). Thus far, a trial-and-error method has to be applied, because there is no chance to predict the sensitivity properties of a selected primer pair.

Since we have worked with same DNA extraction protocol, salt and primer concentration on LAMP reaction, therefore it cannot play a role on LOD. Sometimes, presence of high GC content can help to increase the sensitivity and efficiency of amplification reaction (Kumar et al., 2014; Dieffenbatch et al., 1993). Another essential consideration that affects the LOD is the accuracy of the model used to predict the detected concentration from the raw analytical signals generated from the analytes. In this case, the current obtained from the samples containing the redox molecules was measured. All the blanks and negative samples produced current signals ranging of 50 µA, whereas for the positive samples the signals were significantly larger. Hence, by analyzing the data we could evaluate the minimum amount of meat species DNA required for accurate detection.

This is the first report of pork and chicken species identification using graphene biosensor-based electrochemical detection. A previous study reported the use of LAMP amplicons to identify targeted meat species DNA (pork, chicken and beef), for which they achieved a LOD of 20.33 ng/µL and 78.68 pg/µL for pork and chicken, respectively, using electrochemical detection on carbon biosensors based on DNA-Hoechst 33258 interactions (Ahmed et al., 2009). In comparison, our method is orders of magnitude more sensitive owing to the use of graphene biosensors combined with RuHex molecules for detection. We used the SWV process because of its faster signal acquisition and increased sensitivity compared with other electrochemical methods, and very low measurement variation between replicates was achieved here. Our approach may therefore prove more useful than previous attempts at meat species identification.

We next tested our detection platform using various samples of processed (cooked) foods from different species (Table 1). All samples were collected from the local market of Negara Brunei Darussalam, which is a Southeast Asian country located on the north coast of the island of Borneo. Genomic DNA from these foods were isolated and pork-specific loop primer pairs were used for LAMP amplification. Using appropriate loop primer pairs, target sequences have been amplified from the extracted DNA from the processed foods, and the resulting aplicons were used for identification of the pork species by using graphene biochip for the first time as shown in table 4. The production of LAMP-positive amplicons indicated the presence of pork species in the sample. Pork samples produced high cathodic peaks (>100 µA) compared with the low cathodic peaks (~50 µA) observed for other species (Table 4). Similarly, using the appropriate loop primer pairs for chicken species identification, various processed foods were tested and the resulting amplicons were analyzed using graphene biochip-based detection (Table 5). The previous study was performed with meat species LAMP amplicons where they have found the limit of detection is 20.33 ng/µL and 78.68 pg/µL for pork and chicken respectively (Ahmed et al., 2008; 2009). They have used for their electrochemical analysis, carbon biochip with DNA and Hoechst 33258 interactions. In comparison with this method our method is more sensitive due to the usage of graphene biochips with RuHex molecules (FIG. 5A-B and 6A-B). We have also used SWV process due to its faster signal acquisition and increased sensitivity compared with other electrochemical methods. The measurement was done with each sample for three repetitive times. Error bars indicates the standard deviation (FIG. 3) of those three repeated measurements. From Table 3 it can be said that the variation of the measurement from current is very low. Hence it proves that this method is more sensitive and fruitful for detection process of meat species.

TABLE 4

Meat species identification of processed foods using LAMP, and electrochemical detection using graphene biosensor.

| | Pork loop primers | | |
|---|---|---|---|
| Food Sample | Average current (µA) n = 3 | SD | Detection of Pork |
| Negative control | 50.68 | 0.57 | − |
| Pork sausages | 116.90 | 0.47 | + |
| Curry mutton | 42.16 | 0.54 | − |
| Corned beef | 43.65 | 0.39 | − |
| Chicken luncheon meat (Singapore) | 56.42 | 0.82 | − |
| Chicken luncheon meat (Malaysia) | 50.77 | 0.59 | − |
| Chicken randang | 49.44 | 0.18 | − |
| Canned pork | 124.83 | 3.12 | + |
| Mock curry mutton | 50.33 | 0.47 | − |
| Pork luncheon meat | 116.60 | 0.92 | + |
| Chicken luncheon meat | 45.68 | 0.49 | − |

Meat species identification of processed foods using LAMP combined with electrochemical detection on graphene biochips. Chicken-specific LAMP primers were used for amplification.

| | Chicken loop primers | | |
|---|---|---|---|
| Sample | Average current (µA), n = 3 | SD | LAMP-positive products |
| Negative control | 47.51 | 0.54 | − |
| Pork sausages | 59.16 | 1.25 | − |
| Curry mutton | 50.85 | 1.23 | − |
| Corned beef | 47.16 | 0.68 | − |
| Chicken luncheon meat (Singapore) | 121.08 | 0.87 | + |
| Chicken luncheon meat (Malaysia) | 118.53 | 0.21 | + |
| Chicken randang | 110.42 | 0.88 | + |
| Canned pork | 49.05 | 0.73 | − |
| Mock curry mutton | 48.60 | 0.32 | − |
| Pork luncheon | 47.90 | 0.98 | − |
| Chicken luncheon meat | 126.39 | 1.28 | + |

Optimization of LAMP with Respect to Time Variation: For the first time, we also examined the effect of varying amplification time periods (0, 20, 40 and 60 min) on the detection of chicken and pork amplicons under isothermal conditions, using their respective optimal amplification temperatures. For the negative control, PCR-grade water was used without any template DNA. Pork primers were used with pork DNA as the LAMP-positive reaction, while chicken DNA was used to test for cross-reactivity. A total of 100 pg/µL of the template DNA was used for each reaction. First, the negative control, chicken and pork DNA were amplified at 63° C. over the specified time intervals using pork-specific primers. The LAMP products were then analyzed and detected with the RuHex/SWV electrochemical system, and the results were validated by analysis with 2% agarose gel electrophoresis. The negative control sample and the chicken DNA did not produce any amplicons because of the absence of specific target DNA.

Figure 1A:
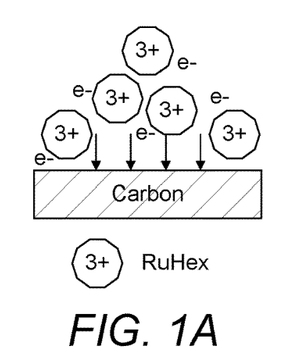
Figure 1B:
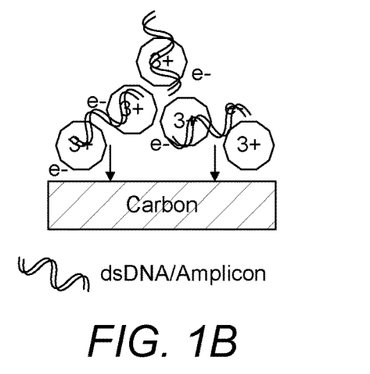
Figure 1C:
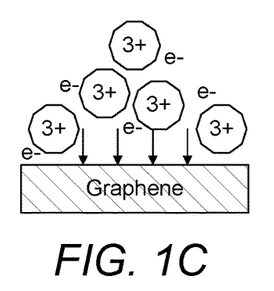
Figure 1D:
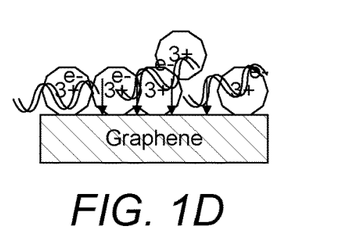
Figure 2:
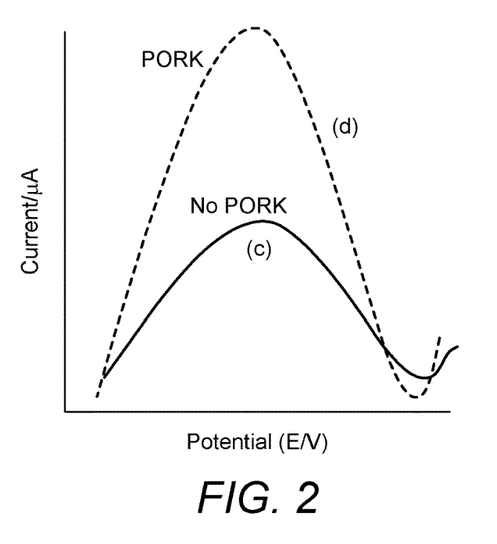
FIG. 2 shows scheme of SWV in higher cathodic peak current in presence of pork specific isothermal amplicon (LAMP product) (d), compared to non-target control (c).
Figure 7:
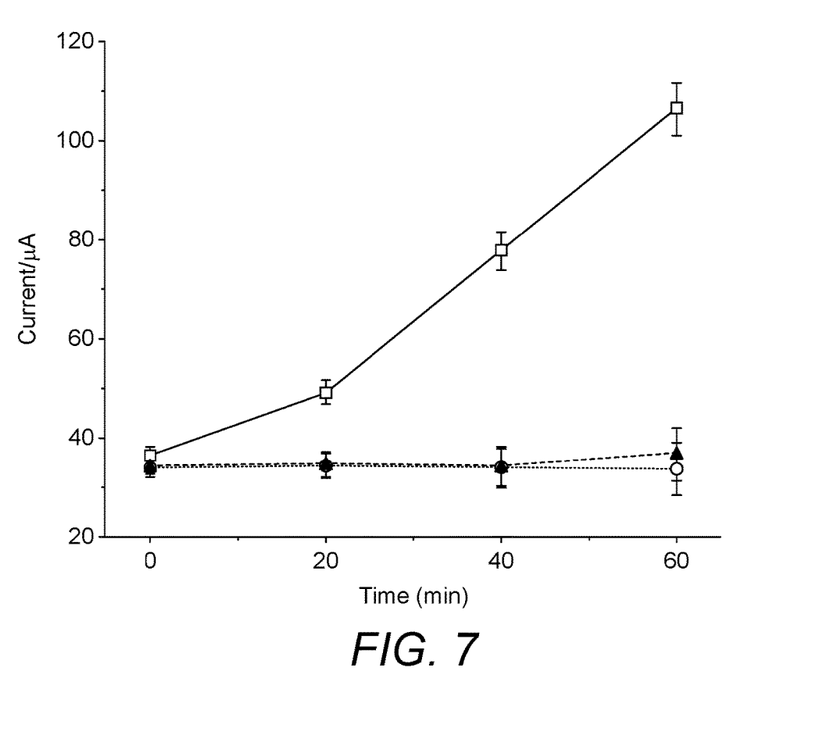
FIG. 7 shows time-dependent monitoring of LAMP amplicons over 60 min incubation at 63° C. Here, 100 pg/μL of template DNA was used for the LAMP reaction along with the pork-specific primers where the template was (a) chicken DNA, (b) negative control (water only), or (c) pork DNA. No LAMP amplicons were detected for (a) or (b) over the 60 min incubation, while electrochemical detection of pork amplicons in (c) was possible from 20 min onwards. Error bars indicate the standard deviation of at least three replicates.

Comparing the results of the two different analysis methods indicated that the isothermal amplicons were indeed being produced, with detectable products visible from the 20$^{th}$ min of amplification: on the agarose gel, a ladder-like pattern was observed from the 40$^{th}$ min (data not shown), whereas with SWV detection, the cathodic peak started to increase and was detected from the 20$^{th}$ min (FIG. 7), reaching the highest level at the 60$^{th}$ min (~100 μA). The amplicons were actually evident from the 20$^{th}$ min on the agarose gel as well; however, the resolution was too low for reproducible visualization. In contrast, the electrochemical sensors were sensitive enough to reproducibly detect the trace amounts of amplicons from the 20$^{th}$ min onwards. Where species-specific isothermal amplicons were detected on carbon biochips using Hoechst 33258 molecules, the anodic peak obtained for the non-target control was higher than in our system, and significantly lower for the specific amplicons (Ahmed et al., 2009). This was due to the DNA-Hoechst 33258 complexes remaining in solution on the carbon biosensor, rather than absorbing to the biosensor surface. In our study, we observed a lower cathodic peak for the non-target control and a comparatively higher cathodic peak for the specific amplicons, attributable to the combined use of the graphene biosensor and RuHex molecules [as shown in FIG. 2, wherein higher cathodic peak current is produced in the presence of pork specific isothermal amplicon (LAMP product) (d) compared to non-target control (c)].

In this report, the overall approach for the specific and sensitive detection of amplicons using SWV and chronocoulometric analysis of the cationic molecule, RuHex, on a graphene-based sensor surface, was evaluated with salmon DNA and pork- and chicken-specific amplicons. The results of the electrochemical and gel electrophoresis analyses of the LAMP amplicons were in complete agreement. This specificity was confirmed with cross-reactivity tests, where only the targeted species were shown to produce LAMP-positive amplicons.

This is the first report of an electrochemical LAMP assay protocol for pork and chicken species detection using DNA-redox electrostatic interactions and DNA-graphene non-specific adsorption phenomena. With this novel assay platform, we achieved a detection limit for chicken and pork species of 1 pg/μL and 100 pg/μL, respectively. This method is highly specific and significantly more sensitive compared with previously reported electrochemical LAMP-based species identification (Ahmed et al., 2009). Our LAMP/graphene biochip-based electrochemical sensor has demonstrated potential for high sensitivity and specificity detection of meat species for the verification of food adulteration (Ahmed et al., 2014). Another advantage of this method is its capacity for rapid detection, because this approach is much less time-consuming compared with conventional PCR-based analysis, which may take up to 2-3 h. We have calculated the Diffusion coefficient of RuHex in presence and absence of DNA onto the electrode surface. According to our calculation, in presence of DNA, peak current was higher due to higher diffusion of RuHex (170.955×10$^8$ cm$^2$/s) onto the graphene electrode. As said, DNA-RuHex interaction caused the complex closed each other and then t stacking brought the complex close to the electrode surface. Whereas, in absence of DNA the diffusion coefficient was lower (27.04×10$^8$ cm$^2$/s) due to dispersed RuHex (but not close to the electrode) in solution and no pi stacking between DNA and graphene. Furthermore, being an isothermal method and thereby avoiding the thermal cycling process, this method has potential for the development of a portable biosensor for on-site monitoring of meat species in processed foods.

In this research, overall approach of the specific and sensitive amplicon detection method based on SWV and chronocoulometric of cationic metal RuHex on the sensor surface, was evaluated by using salmon DNA, pork and chicken specific amplicons. For the first time, we have tried to optimize a new electrochemical LAMP assay protocol for pork and chicken species detection, through utilization of DNA-redox electrostatic interaction and DNA-graphene non-specific adsorption phenomenon. Successfully, we have determined the limit of detection for chicken and pork species of 1 pg/μL and 100 pg/μL, respectively (Table 3). The method, which we have used, is novel, specific and more sensitive as compared to the previously reported electrochemical LAMP based species identification. The results of the LAMP assay and the electrochemical analysis correlated with each other and we have found that LAMP/graphene biochip based electrochemical sensor has the true potential for on-site high sensitivity and specificity detection of the meat species, to verify food adulteration. Another merit of this method was its rapid detection, as it took shorter time as compared to the conventional PCR based analysis, which may take up to two to three hours. Furthermore, being an isothermal method and avoiding the thermal cycling process, the method is a potential contender to become a portable biosensor for on-site monitoring of meat species in the processed foods.

Although the present embodiments have been described with reference to specific example embodiments, it will be evident that various modifications and changes may be made to these embodiments without departing from the broader spirit and scope of the various embodiments.

What is claimed is:

1. A method of using a graphene biosensor to detect a specific species in a food item, comprising:
synthesizing a primer specific for the specific species to be tested in the food item;
preparing a ruthenium hexamine solution;
adsorbing the ruthenium hexamine solution on the surface of graphene biosensor;
contacting the graphene biosensor with the food item to be tested;
allowing the binding of DNA from the species in the food item to the ruthenium hexamine solution;
amplifying the bound DNA using loop mediated isothermal amplification method using the synthesized primer; and
detecting the cathodic current produced by applying voltage by means of square wave voltammetry, such that a higher catholic current is produced indicating presence of DNA in the food item in comparison to the low catholic current indicating an absence of DNA in the food item.

2. The method of claim 1, wherein the ruthenium hexamine binds with free DNA present in the food item indicating presence of specific species in the food item.

3. The method of claim 1, wherein the DNA is detected in picogram level in the food item.

4. A method of using a graphene biosensor to detect a meat species in a food item, comprising:
synthesizing a primer for the meat species to be detected;
preparing a ruthenium hexamine solution;
adsorbing the ruthenium hexamine solution onto the surface of graphene biosensor;
contacting the graphene biosensor with the food item to be tested;
allowing the binding of DNA from the meat species to the ruthenium hexamine solution;
amplifying the bound DNA using loop mediated isothermal amplification method using the synthesized primer; and
detecting the cathodic current produced by applying voltage by means of square wave voltammetry, such that a higher catholic current is produced indicating presence of DNA of the meat species in the food item in comparison to the low catholic current indicating an absence of DNA of the meat species in the food item.

5. The method of claim 4, wherein presence of the DNA is detected at picogram level in the food item.

6. A method of using a graphene biosensor to detect more than one species in a food item, comprising:
synthesizing a primer specific for each species to be tested in the food item;
preparing a ruthenium hexamine solution;
adsorbing the ruthenium hexamine solution on the surface of graphene biosensor;
diluting the food item from 1000 pg to 1 pg;
contacting the graphene biosensor with the food item;
allowing the binding of DNA from each species in the food item to the ruthenium hexamine solution;
amplifying the bound DNA using loop mediated isothermal amplification method using the synthesized primer specific for each species to be tested; and
detecting the cathodic current produced by applying voltage by means of square wave voltammetry, such that a higher catholic current is produced indicating presence of DNA in the food item in comparison to the low catholic current indicating an absence of DNA in the food item.

7. The method of claim 6, wherein primers are synthesized for every species to be detected in the food item.

8. The method of claim 6, wherein the species is one of meat, pork, chicken, or salmon.

9. The method of claim 6, wherein presence of the DNA is detected at picogram level in the food item.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Chicken

<400> SEQUENCE: 1
gccccatcca acatctctg                                                  19

<210> SEQ ID NO 2
<211> LENGTH: 19

```
<212> TYPE: DNA
<213> ORGANISM: Chicken

<400> SEQUENCE: 2
cgtttgcgtg gagattccg                                                    19

<210> SEQ ID NO 3
<211> LENGTH: 42
<212> TYPE: DNA
<213> ORGANISM: Chicken

<400> SEQUENCE: 3
atggctagta gtaggccggt gattcggctc cctattagca gt                          42

<210> SEQ ID NO 4
<211> LENGTH: 42
<212> TYPE: DNA
<213> ORGANISM: Chicken

<400> SEQUENCE: 4
cacagcagac acatccctag cctcagccgt attgtacgtt cc                          42

<210> SEQ ID NO 5
<211> LENGTH: 20
<212> TYPE: DNA
<213> ORGANISM: Chicken

<400> SEQUENCE: 5
ggatttgggt catgaggcag                                                   20

<210> SEQ ID NO 6
<211> LENGTH: 22
<212> TYPE: DNA
<213> ORGANISM: Chicken

<400> SEQUENCE: 6
ttctcctcct ccgtagccca ca                                                22

<210> SEQ ID NO 7
<211> LENGTH: 19
<212> TYPE: DNA
<213> ORGANISM: Pork

<400> SEQUENCE: 7
atcattctga ggagctacg                                                    19

<210> SEQ ID NO 8
<211> LENGTH: 18
<212> TYPE: DNA
<213> ORGANISM: Pork

<400> SEQUENCE: 8
ttgttggatc cggtttcg                                                     18

<210> SEQ ID NO 9
<211> LENGTH: 46
<212> TYPE: DNA
<213> ORGANISM: Pork

<400> SEQUENCE: 9
aagccccctc agattcattc tacgtcatca caaatctact atcagc                      46

<210> SEQ ID NO 10
```

```
<211> LENGTH: 40
<212> TYPE: DNA
<213> ORGANISM: Pork

<400> SEQUENCE: 10
caaagcaacc ctcacacgat tctatgagat gtacggctgc                              40

<210> SEQ ID NO 11
<211> LENGTH: 22
<212> TYPE: DNA
<213> ORGANISM: Pork

<400> SEQUENCE: 11
aggtctgttc cgatataagg at                                                 22

<210> SEQ ID NO 12
<211> LENGTH: 20
<212> TYPE: DNA
<213> ORGANISM: Pork

<400> SEQUENCE: 12
cgccttccac tttatcctgc                                                    20
```